US009499520B2

(12) United States Patent
Burrell et al.

(10) Patent No.: US 9,499,520 B2
(45) Date of Patent: *Nov. 22, 2016

(54) PROCESS FOR THE PREPARATION OF VORICONAZOLE AND ANALOGUES THEREOF

(71) Applicant: Pfizer Ireland Pharmaceuticals, Ringaskiddy, County Cork (IE)

(72) Inventors: Adam James Musgrave Burrell, Dublin (IE); Padraig Mary O'Neill, Dublin (IE); Alan John Pettman, Sandwich (GB)

(73) Assignee: Pfizer Ireland Pharmaceuticals, Ringaskiddy (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/133,621

(22) Filed: Apr. 20, 2016

(65) Prior Publication Data
US 2016/0229842 A1    Aug. 11, 2016

Related U.S. Application Data

(63) Continuation of application No. 14/431,319, filed as application No. PCT/IB2013/059202 on Oct. 8, 2013, now Pat. No. 9,388,167.

(60) Provisional application No. 61/713,761, filed on Oct. 15, 2012.

(51) Int. Cl.
C07D 403/06    (2006.01)
C07D 239/30    (2006.01)

(52) U.S. Cl.
CPC ........... C07D 403/06 (2013.01); C07D 239/30 (2013.01)

(58) Field of Classification Search
CPC ........................... C07D 239/30; C07D 403/06
See application file for complete search history.

(56) References Cited

U.S. PATENT DOCUMENTS 9,388,167 B2 *    7/2016    Burrell ................. C07D 403/06

FOREIGN PATENT DOCUMENTS

WO    2011045807 A2    4/2011
WO    2012171337        12/2012

OTHER PUBLICATIONS

Enantioselective Copper-Catalyzed Reductive Coupling of Alkenylazaarenes with Ketones, Journal of the American Chemical Society, vol. 134, No. 20, May 23, 2012, pp. 8428-8431.
PCT International Search Report, PCT/IB2013/059202, dated Jan. 20, 2014.
English abstract CN1919846A, Novel oriented synthesis method of voriconazole, medicinal salt and intermediate thereof, Feb. 28, 2007, Zhou Huaming, et al.
English abstract WO 94/19327A1, Nucleosides, Their Preparation and Their Use as Therapeutic Agents and as Building Blocks of Synthetic Oligonucleotides, Sep. 1, 1994, Dieter Baerwolff.
English abstract DE19650378A1, New 4-azo- and 4-hydrazino-pyrimidine compounds, Jun. 10, 1998, Eberhard Ammermann, et al.

* cited by examiner

Primary Examiner — Erich A Leeser
(74) Attorney, Agent, or Firm — J. Michael Dixon

(57) ABSTRACT

The present invention provides a process for preparing a compound of formula: (Formula XI and XII) (XI) (XII) wherein X, Y, Z, A, B and E are as defined herein, by reacting a compound of formula: (Formula XIII) (XIII) with a compound of formula: (Formula XIV and XV) (XIV) (XV) respectively, in the presence of a transition metal catalyst, a ligand suitable for use with 15 the catalyst and a reducing agent. The invention also provides novel intermediates.

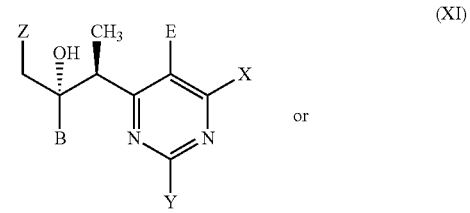

(XI)

or

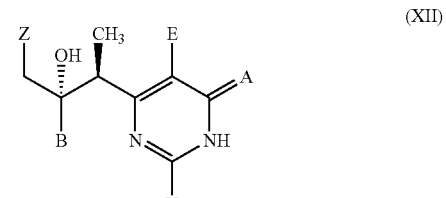
(XII)

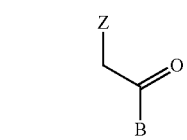

(XIII)

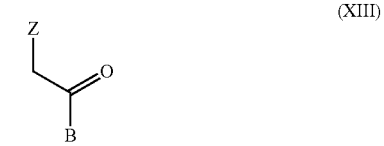

(XIV)

or

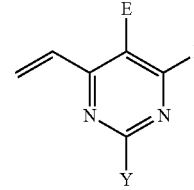

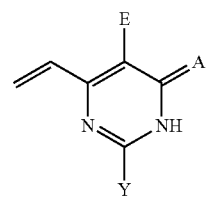
(XV)

10 Claims, No Drawings

PROCESS FOR THE PREPARATION OF VORICONAZOLE AND ANALOGUES THEREOF

CROSS REFERENCE

This application is a continuation of U.S. patent application Ser. No. 14/431,319 filed Mar. 26, 2105 which is the National Stage Application of International Patent Application No. PCT/IB2013/059202, filed Oct. 8, 2013, which claims priority to U.S. Provisional Patent Application Ser. No. 61/713,761, filed Oct. 15, 2012, the contents of which are incorporated by reference.

The present invention relates to an improved process for the preparation of the antifungal drug voriconazole and analogues thereof.

Published European patent application EP 0 357 241 A1 discloses antifungal triazoles of formula:

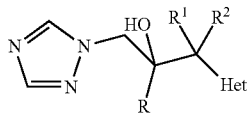

and pharmaceutically acceptable salts thereof, wherein R is phenyl optionally substituted by 1 to 3 substituents each independently selected from halo and $CF_3$; $R^1$ is $C_1$-$C_4$ alkyl; $R^2$ is H or $C_1$-$C_4$ alkyl; and Het, which is attached to the adjacent carbon atom by a ring carbon atom, is selected from pyridinyl, pyridazinyl, pyrimidinyl, pyrazinyl and triazinyl, said Het being optionally substituted by $C_1$-$C_4$ alkyl, $C_1$-$C_4$ alkoxy, halo, $CF_3$, CN, $NO_2$, $NH_2$, —NH($C_1$-$C_4$ alkanoyl) or —NHCO$_2$($C_1$-$C_4$ alkyl). It is disclosed that the compounds may be prepared by (a) deprotonating a compound of formula:

with a strong base and reacting it with a ketone of formula:

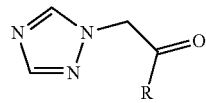

or (b) reacting an epoxide of formula:

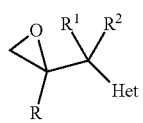

or a compound bearing a leaving group Y of formula:

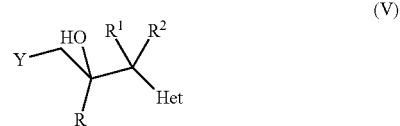

with triazole.

Published European patent application EP 0 440 372 A1 discloses a group of fungicidal triazoles having the formula

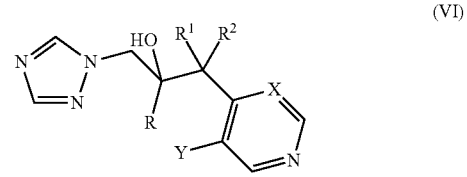

wherein R is phenyl substituted by 1 to 3 substituents each independently selected from halo, —$CF_3$, and —$OCF_3$; $R^1$ is $C_1$-$C_4$ alkyl; $R^2$ is H or $C_1$-$C_4$ alkyl; X is CH or N; and Y is F or Cl. It is disclosed that the compounds may be prepared by the same routes described above in relation to the compounds of formula (I). A further route is proposed wherein a compound of formula (VII)

bearing one or two reducible groups $Z^2$ and $Z^3$ (e.g. chloro groups) is reduced, for example by hydrogenolysis.

One of the specific compounds disclosed in EP 0 440 372 A1 is (2R,3S)-2-(2,4-difluorophenyl)-3-(5-fluoropyrimidin-4-yl)-1-(1H-1,2,4-triazol-1-yl)butan-2-ol of formula:

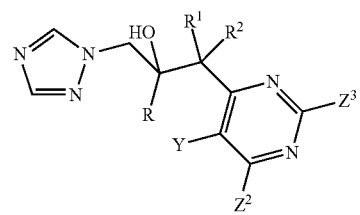

(see Examples 7-9). This compound is known generically as voriconazole and has been commercialised under the trade name VFEND® for the treatment of fungal infections.

International patent publication WO-1997/06160 A1 discloses a process for preparing a compound of formula

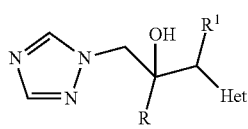

(IX)

in which R is phenyl optionally substituted by 1 to 3 substituents each independently selected from halo and trifluoromethyl; $R^1$ is $C_1$-$C_6$ alkyl; and Het is pyrimidinyl optionally substituted by 1 to 3 substituents independently selected from $C_1$-$C_4$ alkyl, $C_1$-$C_4$ alkoxy, halo, oxo, benzyl and benzyloxy; in which a compound of formula (III) (see above) is reacted with a compound of formula:

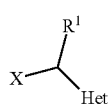

(X)

in which X is chloro, bromo or iodo, in the presence of zinc, iodine and/or a Lewis acid. The reaction may also be performed with one or two additional chloro or bromo atoms on the Het which are subsequently removed by reduction (e.g. hydrogenolysis).

Voriconazole is a single (2R,3S) stereoisomer and control of both relative and absolute stereochemistry is therefore an important goal in any synthetic method designed for its preparation. The processes described above are able to impart varying degrees of relative stereochemical control in the construction of the two adjacent stereocentres but none are able to impart absolute stereocontrol of any kind. Thus, for instance, in Example 7 of published European patent application EP 0 440 372 A1, voriconazole is prepared as a racemate which is resolved using 1R-(–)-10-camphorsulphonic acid in order to provide the pure (2R,3S) enantiomer. It would be advantageous to provide a process for the preparation of voriconazole which controlled both the relative and absolute stereochemistry of the two chiral centres and provided the (2R,3S) stereoisomer directly. Attempts to control the absolute stereochemistry of the Reformatsky process described in EP 0 440 372 A1 by the addition of chiral ligands, however, have been unsuccessful.

It has been reported in the literature that the addition of certain copper-based nucleophiles to ketones can be made to proceed in an enantioselective fashion by utilising chiral ligands. Thus, for example, copper nucleophiles have been generated from α,β-unsaturated ketones, esters and thioesters and added to aldehydes and ketones enantioselectively (Tetrahedron Letters, 2012, 53, 4199-4201; Chem. Asian J., 2010, 5, 478; Chem. Commun., 2008, 4309-4311; J. Am. Chem. Soc., 2008, 130(9), 2747; J. Am. Chem. Soc., 2008, 130, 14378-14379; Org. Biomol. Chem., 2011, 9, 6143-6147; Org. Biomol. Chem., 2012, 10, 5971-5978; Org. Letters, 2006, 8(26), 6059-6062); Org. Letters, 2006, 8(26), 5943-5946; Angew. Chem. Int. Ed., 2006, 45, 1292-1297; Synlett., 2009, 8, 1299-1302; Tetrahedron Lett., 2006, 47, 1403-1407). The enantioselective addition to ketones of copper nucleophiles generated from allenes has also been demonstrated (J. Am. Chem. Soc., 2006, 128, 14440-14441; Tetrahedron Lett., 2006, 47, 1403-1407). More recently, the generation of copper nucleophiles from certain vinyl heteroaromatic compounds and their addition to a range of ketones has been reported (J. Am. Chem. Soc., 2012, 134, 8428). None of these references, however, discloses the generation of a copper nucleophile from a 4-vinyl pyrimidine and its enantioselective addition to a ketone. Nor do they disclose the addition of any copper nucleophile to a phenyl methyl ketone bearing a substituent on the methyl group.

The present invention provides a process for preparing a compound of formula:

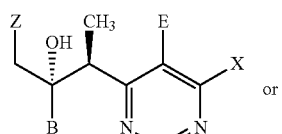

(XI)

or

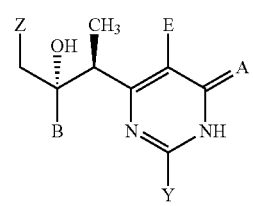

(XII)

wherein:
X is H, halo, —$NH_2$, —$NH(C_1$-$C_6$ alkyl), —$N(C_1$-$C_6$ alkyl)($C_1$-$C_6$ alkyl), —$Si(R^3)_3$ [wherein $R^3$ is, independently in each case, $C_1$-$C_6$ alkyl, aryl or aryl($C_1$-$C_6$ alkyl)], —$O(C_1$-$C_6$ alkyl), —O-aryl, —$S(C_1$-$C_6$ alkyl), —$OSO_2(C_1$-$C_6$ alkyl), —$NHSO_2(C_1$-$C_6$ alkyl) or —S-aryl; Y is H, halo, —$NH_2$, —$NH(C_1$-$C_6$ alkyl), —$N(C_1$-$C_6$ alkyl)($C_1$-$C_6$ alkyl), —$Si(R^3)_3$ [wherein $R^3$ is as defined above], —$O(C_1$-$C_6$ alkyl), —O-aryl, —$S(C_1$-$C_6$ alkyl), —$OSO_2(C_1$-$C_6$ alkyl), —$NHSO_2(C_1$-$C_6$ alkyl) or —S-aryl;
Z is optionally substituted heteroaryl, —$Si(R^3)_3$ (wherein $R^3$ is as defined above), —OH, a protected hydroxyl group, halo, nitro, cyano, —SH, a protected thio group, $C_1$-$C_6$ alkyl or $C_1$-$C_6$ alkoxy;
A is O, S or NH;
B is phenyl substituted by one or more halo atoms; and
E is a halo atom;
by reacting a compound of formula:

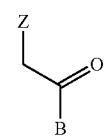

(XIII)

wherein Z and B are as defined above, with a compound of formula:

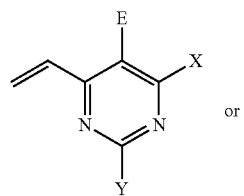

(XIV)

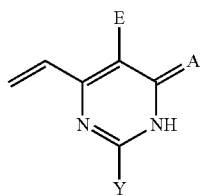

(XV)

respectively, wherein X, Y, A and E are as defined above, in the presence of a transition metal catalyst, a ligand suitable for use with the catalyst and a reducing agent. This kind of reaction is commonly described as a reductive aldol condensation. The generation of a transition metal nucleophile from a 4-vinylpyrimidine and its addition to a substituted acetophenone is unprecedented.

The relative stereochemistry that is obtained is shown in formulae (XI) and (XII). If an achiral ligand is used then the product will be racemic. If a chiral ligand is used, on the other hand, the reaction proceeds enantioselectively.

When Z is a heteroaryl group it is preferably either (i) a 6-membered aromatic heterocycle containing 1-3 N atoms or (ii) a 5-membered aromatic heterocycle containing either (a) 1-4 N atoms or (b) 1 O or S atom and 0-3 N atoms. Heteroaryl groups may be attached via a ring carbon atom (in all cases) or a ring nitrogen atom with an appropriate valency. When substituted, the substituent may be located on a ring carbon atom (in all cases) or a ring nitrogen atom with an appropriate valency (if the substituent is joined through a carbon atom). Specific examples of heteroaryl include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridyl, pyridazinyl, pyrimidinyl and pyrazinyl. Possible substituents include $C_1$-$C_6$ alkyl, $C_3$-$C_8$ cycloalkyl, halo, —CN, —$NO_2$, —O($C_1$-$C_6$ alkyl), —N($C_1$-$C_6$ alkyl)($C_1$-$C_6$ alkyl), —S($C_1$-$C_6$ alkyl), —SO($C_1$-$C_6$ alkyl), —$SO_2$($C_1$-$C_6$ alkyl), —CO($C_1$-$C_6$ alkyl), —OCO ($C_1$-$C_6$ alkyl), —COO($C_1$-$C_6$ alkyl), —N($C_1$-$C_6$ alkyl)CO ($C_1$-$C_6$ alkyl), —CON($C_1$-$C_6$ alkyl)($C_1$-$C_6$ alkyl), —N($C_1$-$C_6$ alkyl)$SO_2$($C_1$-$C_6$ alkyl), —$SO_2$N($C_1$-$C_6$ alkyl)($C_1$-$C_6$ alkyl), —N($C_1$-$C_6$ alkyl)CON($C_1$-$C_6$ alkyl)($C_1$-$C_6$ alkyl), —N($C_1$-$C_6$ alkyl)COO($C_1$-$C_6$ alkyl) and —N($C_1$-$C_6$ alkyl)$SO_2$N($C_1$-$C_6$ alkyl)($C_1$-$C_6$ alkyl).

In the case where Z is a protected hydroxy or thio group, suitable protecting groups are well known to the skilled person from his or her common general knowledge. See, for instance, 'Protective Groups in Organic Chemistry' by Wuts and Greene (Wiley-Blackwell). Preferred protecting groups are trialkylsilyl groups, such as trimethylsilyl and tert-butyldimethylsilyl, and arylmethyl groups such as benzyl.

Aryl means phenyl or naphthyl, said phenyl and naphthyl being optionally substituted with 1-5 substituents each independently selected from $C_1$-$C_6$ alkyl, $C_3$-$C_8$ cycloalkyl, halo, —CN, —$NO_2$, —O($C_1$-$C_6$ alkyl), —N($C_1$-$C_6$ alkyl)($C_1$-$C_6$ alkyl), —S($C_1$-$C_6$ alkyl), —SO($C_1$-$C_6$ alkyl), —$SO_2$($C_1$-$C_6$ alkyl), —CO($C_1$-$C_6$ alkyl), —OCO($C_1$-$C_6$ alkyl), —COO ($C_1$-$C_6$ alkyl), —N($C_1$-$C_6$ alkyl)CO($C_1$-$C_6$ alkyl), —CON ($C_1$-$C_6$ alkyl)($C_1$-$C_6$ alkyl), —N($C_1$-$C_6$ alkyl)$SO_2$($C_1$-$C_6$ alkyl), —$SO_2$N($C_1$-$C_6$ alkyl)($C_1$-$C_6$ alkyl), —N($C_1$-$C_6$ alkyl)CON($C_1$-$C_6$ alkyl)($C_1$-$C_6$ alkyl), —N($C_1$-$C_6$ alkyl)COO($C_1$-$C_6$ alkyl) and —N($C_1$-$C_6$ alkyl)$SO_2$N($C_1$-$C_6$ alkyl)($C_1$-$C_6$ alkyl).

The term "alkyl", alone or in combination, means an acyclic, saturated hydrocarbon group of the formula $C_nH_{2n+1}$ which may be linear or branched. Examples of such groups include methyl, ethyl, n-propyl, isopropyl, n-butyl, isobutyl, sec-butyl, tert-butyl, pentyl, iso-amyl and hexyl. Unless otherwise specified, an alkyl group comprises from 1 to 6 carbon atoms.

The term "alkoxy" means an alkyl group joined through an oxygen atom, e.g. methoxy ($CH_3$—O—), ethoxy ($CH_3CH_2$—O—).

The carbon atom content of alkyl and various other hydrocarbon-containing moieties is indicated by a prefix designating a lower and upper number of carbon atoms in the moiety, that is, the prefix $C_i$-$C_j$ indicates a moiety of the integer "i" to the integer "j" carbon atoms, inclusive. Thus, for example, $C_1$-$C_6$ alkyl refers to alkyl of one to six carbon atoms, inclusive.

The term "halo" means, fluoro, chloro, bromo or iodo.

Preferably, Z is optionally substituted heteroaryl or chloro.

Most preferably, Z is 1,2,4-triazol-1-yl.

Preferably, X is chloro and Y is H.

Preferably, B is 2,4-difluorophenyl.

Preferably, E is fluoro.

In one particularly preferred embodiment, Z is 1,2,4-triazol-1-yl; X is chloro; Y is H; B is 2,4-difluorophenyl and E is fluoro.

More preferably still, the invention provides a process for preparing a compound of formula:

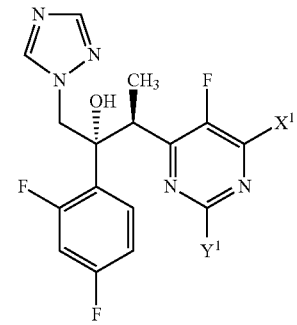

(XVI)

wherein $X^1$ and $Y^1$ are both H or one of $X^1$ and $Y^1$ is H and the other is chloro;

by reacting a compound of formula:

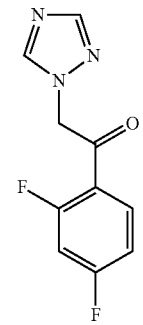

(XVII)

with a compound of formula:

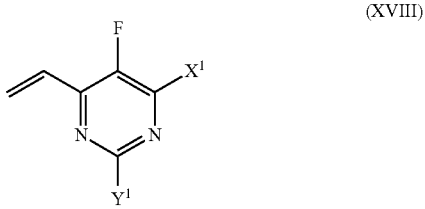

(XVIII)

wherein $X^1$ and $Y^1$ are as defined above, in the presence of a copper catalyst, a chiral phosphine ligand and a reducing agent.

Preferably, the reaction is carried out at a temperature of from −30° C. to +80° C., most preferably at a temperature of from −12° C. to 0° C. A temperature of about −9° C. is optimal.

The reaction is performed in the presence of an organic solvent. An alcohol is preferred. Most preferred is a tertiary alcohol, the optimal solvent being 2-methyl-2-butanol. Examples of suitable solvents include tetrahydrofuran, methyltetrahydrofuran, dimethoxyethane, diethoxyethane, methanol, ethanol, 2-propanol, isopropylacetate, ethylacetate, n-butylacetate, toluene, tetralin, n-butanol, tert-butanol, benzyl alcohol, 1-pentanol, 3-pentanol, 1-hexanol, 2-hexanol, 1-heptanol, 2-heptanol, 4-heptanol, 1-nonanol, 1-methylcyclohexanol, 2-methyl-1-butanol, 2-methyl-2-butanol, 3-methyl-3-pentanol, 3-ethyl-3-pentanol, 2,4-dimethyl-3-pentanol, 1,2-propanediol, 2,3-dimethyl-3-pentanol, anisole, n-butoxyethanol, dichloromethane, tributylamine, N-methylpyrrolidone, acetonitrile, acetone, dimethylsulfoxide and dioxane.

Optionally, the reaction can be performed in the presence of up to 10 equivalents of water (based on the limiting reactant).

Suitable transition metal catalysts are well known to the skilled person from the common general knowledge (see, for instance, J. Am. Chem. Soc., 1999, 121(51), 12202-12203). The transition metal catalyst is preferably a palladium catalyst (see, for example, Tetrahedron Lett., 1998, 39, 5237-5238), a cobalt catalyst (see, for instance, Chem., Lett., 1989, 2005-2008), a nickel catalyst (see, for instance, Org. Lett., 2007, 9(3), 537-540), an iridium catalyst (see, for example, Org, Lett., 2001, 12(3), 1829-1831), an indium catalyst (see, for example, Adv. Synth. Catal., 2002, 344, 283-287; Angew. Chem. Int. Ed., 2004, 43, 711-714), a rhodium catalyst (see, for example, Eur. J. Org. Chem., 2006, 5594-5600) or a copper catalyst, most preferably a copper catalyst.

A preferred copper catalyst is a stable copper(I) or copper (II) salt. If a copper(II) salt is used, sodium tert-butoxide should be added to the reaction mixture. In general, copper (I) salts are preferred, particularly $CuF(PPh_3)_3.MeOH$ ($CuF(PPh_3)_3$.methanol solvate), $CuF(PPh_3)_3.EtOH$ ($CuF(PPh_3)_3$.ethanol solvate) and $CuO^tBu$. Examples of suitable copper(II) salts include $CuCl_2$ and $Cu(OCOCH_3)_2$. Methanol and ethanol solvates of $CuF(PPh_3)_3$ typically contain between 1 and 2 molar equivalents of solvent and are commercially available. For the preparation and use of $CuO^tBu$, see J. Am. Chem. Soc., 1972, 94, 658 and Angew Chemie, 2008, 47, 9961.

The optimal copper catalyst is a solvate of $CuF(PPh_3)_3$ such as $CuF(PPh_3)_3$.methanol solvate or $CuF(PPh_3)_3$.ethanol solvate, particularly $CuF(PPh_3)_3$.methanol solvate.

A catalyst loading of from 0.1 mol % to 2.5 mol % (with respect to the limiting reactant) is preferred. A particularly preferred loading is from 0.1 mol % to 0.5 mol %. The optimal loading is from 0.1 mol % to 0.2 mol %.

A ligand suitable for use with the transition metal catalyst chosen can easily be selected by the skilled person according to his or her common general knowledge (see, for instance, Heterobidentate and Monodentate Phosphine Ligands for Asymmetric Catalysis by Suzanna Christine Milheiro, Yale University, 2011 or Phosphorus(III) Ligands in Homogeneous Catalysis: Design and Synthesis edited by Kamer and van Leeuwen, Wiley 2012). The use of an achiral ligand such as BINAP will lead to the synthesis of a racemic product. The use of a chiral ligand, on the other hand, will lead to an enantioselective synthesis. A preferred ligand is a phosphine ligand. Most preferred is a chiral phosphine ligand.

Most chiral phosphine ligands that are suitable for use with a copper catalyst give excellent results in the reaction. Specific examples of suitable chiral ligands include: (R)-1-[(SP)-2-(diphenylphosphino)ferrocenyl]ethyldi-tert-butylphosphine; (R)-1-[(SP)-2-(dicyclohexylphosphino)ferrocenyl]ethyldicyclohexylphosphine; (R)-1-[(SP)-2-(dicyclohexylphosphino)ferrocenylethyl]diphenylphosphine; (R)-1-[(SP)-2-(diphenylphosphino)ferrocenyl]ethyldi(3,5-xylyl)phosphine; (R)-1-{(SP)-2-[bis[3,5-bis(trifluoromethyl)phenyl]phosphino]ferrocenyl}ethyldicyclohexylphosphine; (R)-1-{(SP)-2-[bis(4-methoxy-3,5-dimethylphenyl)phosphino]ferrocenyl}ethyldicyclohexylphosphine; (R)-1-{(SP)-2-[bis[3,5-bis(trifluoromethyl)phenyl]phosphino]ferrocenyl}ethyldi(3,5-xylyl)phosphine; (R)-1-[(SP)-2-(dicyclohexylphosphino)ferrocenyl]ethyldi-tert-butylphosphine; (R)-1-{(SP)-2-[bis[4-(trifluoromethyl)phenyl]phosphino]ferrocenyl}ethyldi-tert-butylphosphine; (R)-1-{(SP)-2-[bis(4-methoxy-3,5-dimethylphenyl)phosphino]ferrocenyl}ethyldi-tert-butylphosphine; (R)-1-{(SP)-2-[di(2-furyl)phosphino]ferrocenyl}ethyldi(3,5-xylyl)phosphine; (R)-1-{(SP)-2-[di(2-furyl)phosphino]ferrocenyl}ethyldi-tert-butylphosphine; (R)-1-{(SP)-2-[di(1-naphthyl)phosphino]ferrocenyl}ethyldi-tert-butylphosphine; (R)-1-{(SP)-2-[di(1-naphthyl)phosphino]ferrocenyl}ethyldi(3,5-xylyl)phosphine; (R)-1-{(SP)-2-[bis(4-methoxy-3,5-dimethylphenyl)phosphino]ferrocenyl}-ethyldi(3,5-xylyl)phosphine; (R)-1-{(SP)-2-[bis(4-methoxy-3,5-dimethylphenyl)phosphino]ferrocenyl}-ethylbis(2-methylphenyl)phosphine; (R)-1-{(SP)-2-[di(2-furyl)phosphino]ferrocenyl}ethylbis(2-methylphenyl)phosphine; (R)-1-[(SP)-2-(di-tert-butylphosphino)ferrocenyl]ethyldiphenylphosphine; (R)-1-[(SP)-2-(di-tert-butylphosphino)ferrocenyl]ethylbis(2-methylphenyl)phosphine; (R)-(+)-(6,6'-dimethoxybiphenyl-2,2'-diyl)bis(diphenylphosphine); (R)-(6,6'-dimethoxybiphenyl-2,2'-diyl)bis[bis(3,5-di-tert-butyl-4-methoxyphenyl)phosphine; (SP,S'P)-1,1'-bis[(R)-α-(dimethylamino)benzyl]-2,2'-bis(diphenylphosphino)ferrocene; (SP,S'P)-1,1'-bis(dicyclohexylphosphino)-2,2'-bis[(R)-α-(dimethylamino)benzyl]ferrocene; (SP,S'P)-1,1'-bis{bis[3,5-bis(trifluoromethyl)phenyl]phosphino}-2,2'-bis[(R)-α-(dimethylamino)benzyl]ferrocene; (SP,S'P)-1,1'-bis[bis(4-methoxy-3,5-dimethylphenyl)phosphino]-2,2'-bis[(R)-α-(dimethylamino)benzyl]ferrocene; (SP,S'P)-1,1'-bis[(R)-α-(dimethylamino)benzyl]-2,2'-bis[di(3,5-xylyl)phosphino]ferrocene; (SP,S'P)-1,1'-bis[bis(2-methylphenyl)phosphino]-2,2'-bis[(R)-α-(dimethylamino)benzyl]ferrocene; (RP)-1-[(R)-α-(dimethylamino)-2-(diphenylphosphino)benzyl]-2-diphenylphosphinoferrocene; (RP)-1-dicyclohexylphosphino-2-[(R)-α-(dimethylamino)-2-(dicyclohexylphosphino)benzyl]ferrocene; (R)-1-{(RP)-2-[2-(diphenylphosphino)phenyl]ferrocenyl}ethylbis[3,5-bis-(trifluoromethyl)phenyl]phosphine; (R)-1-{(RP)-2-[2-(diphenylphosphino)phenyl]ferrocenyl}ethyldiphenylphosphine; (R)-1-{(RP)-2-[2-

(diphenylphosphino)phenyl]ferrocenyl}ethyldicyclohexylphosphine; (R)-1-{(RP)-2-[2-[bis(4-methoxy-3,5-dimethylphenyl)phosphino]phenyl]ferrocenyl}ethylbis[3,5-bis(trifluoromethyl)phenyl]phosphine; (R)-1-{(RP)-2-[2-(diphenylphosphino)phenyl]ferrocenyl}ethyldi(3,5-xylyl)phosphine; (R)-1-{(RP)-2-[2-(dicyclohexylphosphino)phenyl]ferrocenyl}ethylbis[3,5-bis(trifluoromethyl)phenyl]phosphine; (R)-1-{(RP)-2-[2-[di(3,5-xylyl)phosphino]phenyl]ferrocenyl}ethyldi(3,5-xylyl)phosphine; (R)-1-{(RP)-2-[2-(diphenylphosphino)phenyl]ferrocenyl}ethyldi(2-norbornyl)phosphine; (1R,1'R,2S,2'S)-2,2'-di-tert-butyl-2,3,2',3'-tetrahydro-1H,1'H-(1,1) biisophosphindolyl; (1S,1S',2R,2R')-1,1'-di-tert-butyl-(2,2')-diphospholane; (+)-1,2-bis[(2S,5S)-2,5-dimethylphospholano]benzene; [N-[(1R,2R)-2-(amino-κN)-1,2-(2R,3R)-(+2,3-bis(diphenylphosphino)-bicyclo[2.2.1]hept-5-ene; (R)-(+)-2,2',6,6'-tetramethoxy-4,4'-bis(di(3,5-xylyl)phosphino)-3,3'-bipyridine; (S)-(+)-(3,5-dioxa-4-phosphacyclohepta[2,1-a:3,4-a']dinaphthalen-4-yl) piperidine; (R)-2,2-binaphthoyl-(S,S)-di(1-phenylethyl) aminoylphosphine; (−)-1,2-bis[(2R,5R)-2,5-dimethylphospholano]benzene; (+1,2-bis[(2S,5S)-2,5-dimethylphospholano]ethane; (R)-(+)-5,5'-dichloro-2,2'-bis(diphenylphosphino)-6,6'-dimethoxy-1,1'-biphenyl; (R)-(+)-(1,1'-binaphthalene-2,2'-diyl)bis(diphenylphosphine).

A preferred chiral phosphine ligand is (S)-1-{(S$_P$)-2-[2-(diphenylphosphino)phenyl]ferrocenyl}ethylbis[3,5-bis-(trifluoromethyl)phenyl]phosphine.

Aside from phosphine ligands, other ligands of note include N-heterocyclic carbene ligands (particularly for use with copper; see, for example, Org. Lett., 2006, 8(26), 6059-6062), phosphoramidite and phosphonite ligands (particularly for use with rhodium; see, for example, J. Am. Chem. Soc., 2008, 130, 2746-2747 and Synthesis, 2011, 13, 2011-2013) and bisoxazoline (box) and bisoxazolinylpyridine (pybox) ligands (particularly for use with iridium and rhodium; see, for example, Org. Lett., 2001, 12(3), 1829-1831 and Tetrahedron, 2008, 64, 9408-9412).

The amount of ligand used should be at least one molar equivalent with respect to the amount of transition metal catalyst used. A molar catalyst:ligand ratio of from 1:1 to 1:6 is preferred, a molar ratio of from 1:2 to 1:3 being especially preferred.

The reducing agent must be capable of generating a transition metal hydride (e.g. copper(I)hydride) in situ. A preferred reducing agent is a silane, such as phenylsilane, dimethylphenylsilane, triethoxysilane, tetramethyldisiloxane, diphenylsilane or polymethylhydrosiloxane. A preferred silane is phenylsilane. Other reducing agents which may be employed include pinacolborane. Preferably, the amount of reducing agent used is from 0.5 to 3 equivalents, based on the limiting reactant.

The reaction is diastereoselective in all cases, giving predominantly the relative stereochemistry at the two chiral centres as illustrated in Formulae (XI) and (XII). Typically, greater than 86% of this diastereomer is formed (a diastereomeric excess of 76% or more). When a chiral ligand is used, the product is obtained as predominantly a single stereoisomer. An enantiomeric excess of over 50% is usually achieved, an enantiomeric excess of over 90% being not uncommon.

Where a compound of formula (XVI) in which X$^1$ and Y$^1$ are both H is prepared, the product of the reaction is voriconazole. Where one of X$^1$ and Y$^1$ is chloro, the product may easily be converted to voriconazole by reduction, e.g. by the hydrogenolysis procedure described in EP 0 440 372 A1. Such a hydrogenation is preferably run at a temperature of from 20° C. to 80° C., most preferably at a temperature of from 40° C. to 70° C., for instance at about 40° C. A preferred catalyst is palladium on carbon. The hydrogenation can be performed on the crude reaction mixture from the reductive aldol condensation but in a preferred embodiment said crude reaction mixture is partitioned between toluene and a mild aqueous acid (e.g. aqueous citric acid) and the aqueous layer discarded prior to hydrogenation. Suitable solvents for the hydrogenation step include toluene, ethyl acetate, 3-methyl-3-pentanol and 2-methyl-2-butanol.

The reaction may be run in various other ways to give a product which may be converted to voriconazole by simple functional group conversion. For instance, group B in a compound of formula (XIII) may be 2-chloro-4-fluorophenyl, 2,4-difluorophenyl or 2,4-dichlorophenyl and the chloro atoms or may be converted to fluoro atoms by displacement. Equally, group E in a compound of formula (XI) or (XII) may be a chloro atom which is converted to fluoro by displacement. Such a displacement is illustrated by the procedures described in J. Med. Chem., 2011, 54, 8343-8352 and Tet, Lett., 2010, 2652-2654. Alternatively, B in a compound of formula (XIII) may be a 2,4-fluorophenyl group bearing one or more additional chloro groups which may later be removed by hydrogenation.

The crude voriconazole prepared using these procedures may be conveniently purified by treating a solution of the crude product with an acid in order to precipitate the corresponding salt and subsequent neutralisation of the salt with a base such as sodium acetate. The use of a sulfonic acid is preferred. Camphor sulfonic acid is particularly preferred. Suitable solvents for the precipitation step include toluene, ethyl acetate, methanol, ethanol, 2-propanol, water, acetone, methyl ethyl ketone, methyl isobutyl ketone, tetrahydrofuran and mixtures thereof. A preferred solvent is a mixture of toluene, water and acetone. If a chiral sulfonic acid is used (e.g. camphor sulfonic acid), the enantiomeric excess of the product may be further enhanced, typically to a level of 98-100%.

The present invention also relates to novel intermediates of formula:

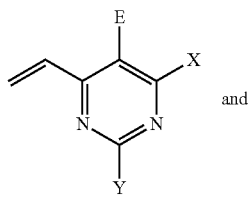

(XIV)

and

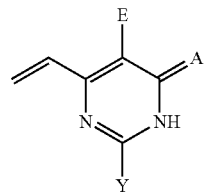

(XV)

wherein
X is H, halo, —NH$_2$, —NH(C$_1$-C$_6$ alkyl), —N(C$_1$-C$_6$ alkyl)(C$_1$-C$_6$ alkyl), —Si(R$^3$)$_3$ [wherein R$^3$ is, independently in each case, C$_1$-C$_6$ alkyl, aryl or aryl(C$_1$-C$_6$ alkyl)], —O(C$_1$-C$_6$ alkyl), —O-aryl, —S(C$_1$-C$_6$ alkyl), —OSO$_2$(C$_1$-C$_6$ alkyl), —NHSO$_2$(C$_1$-C$_6$ alkyl) or —S-aryl;
Y is H, halo, —NH$_2$, —NH(C$_1$-C$_6$ alkyl), —N(C$_1$-C$_6$ alkyl)(C$_1$-C$_6$ alkyl), —Si(R$^3$)$_3$ [wherein R$^3$ is as defined above], —O(C$_1$-C$_6$ alkyl), —O-aryl, —OSO$_2$(C$_1$-C$_6$ alkyl), —NHSO$_2$(C$_1$-C$_6$ alkyl) or —S-aryl;
A is O, S or NH; and
E is a halo atom;
with the proviso that the compound of formula (XIV) is not 5-bromo-4-vinylpyrimidine.

The following Examples illustrate how the procedures described above may be implemented in practice.

EXAMPLE 1

Preparation of Voriconazole

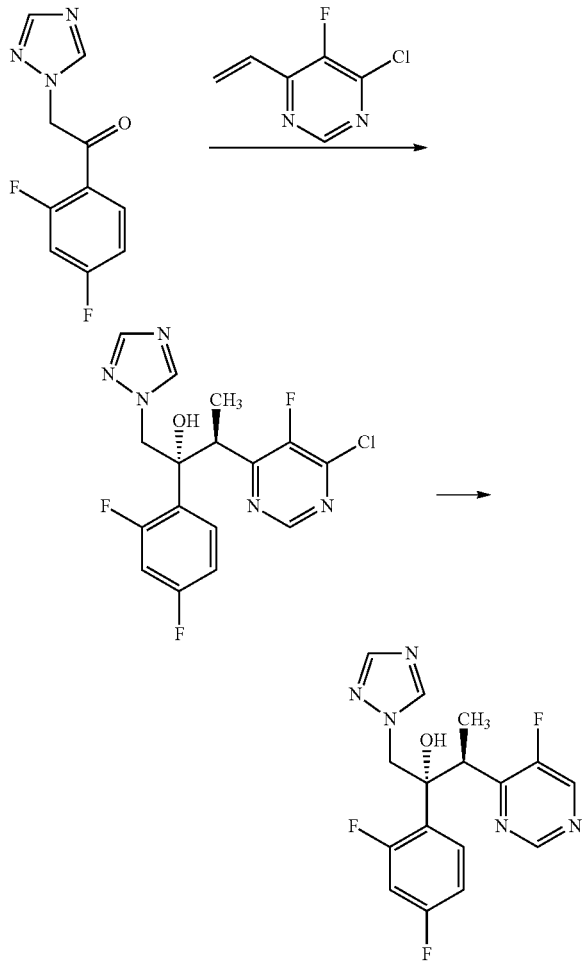

Step 1

To a mixture of CuF(PPh$_3$)$_3$ methanol solvate (0.019 g) and (S)-1-{(S$_P$)-2-[2-(diphenylphosphino)phenyl]ferrocenyl}ethylbis[3,5-bis-(trifluoromethyl)phenyl]phosphine (0.093 g) was added 2-methyl-2-butanol (16 mL). The mixture was stirred at room temperature, under nitrogen, for 30 minutes until all solids were dissolved. To the resulting solution was then added 1-(2,4-difluorophenyl)-2-(1H-1,2,4-triazol-1-yl)ethanone (2.69 g) and water (0.36 g). The reaction slurry was then stirred at room temperature for 20 minutes before being cooled to −9° C.

To the reaction slurry at −9° C. was then added a solution of 4-chloro-5-fluoro-6-vinylpyrimidine (1.59 g, limiting reagent) and phenylsilane (1.09 g) in 2-methyl-2-butanol (4 mL) over 45 minutes. After stirring at −9° C. for 270 minutes, at which time no 4-chloro-5-fluoro-6-vinylpyrimidine was observable by HPLC analysis, the reaction mixture was warmed to room temperature and held at that temperature for 18 hours. Water (3.98 g) was then added to quench the reaction. Toluene (30 mL) was then added to the quenched reaction mixture to give a biphasic mixture containing (2R,3S)-3-(6-chloro-5-fluoropyrimidin-4-yl)-2-(2,4-difluorophenyl)-1-(1H-1,2,4-triazol-1-yl)butan-2-ol.

Solvent was removed in vacuo at 45-50° C. until a residue of approximately 8 mL was achieved. To this was added further toluene (50 mL), followed by 50 mL aqueous citric acid (20% w/v). The biphasic mixture was stirred at room temperature for 30 minutes and the layers were then allowed to separate for 20 minutes. The aqueous layer was discarded and to the toluene layer was added further aqueous citric acid solution (50 mL, 20% w/v). The biphasic mixture was stirred for 10 minutes and the layers were then allowed to separate for 20 minutes. Again, the aqueous layer was discarded. To the toluene layer was added water (9.5 mL). The biphasic mixture was stirred for 10 minutes, allowed to separate (20 minutes) and separated.

To the retained toluene layer was added activated carbon (0.192 g). The mixture was then heated to 50° C. for 3 hours before cooling to room temperature. Palladium on carbon catalyst (Evonik E101 NE/W 10% Pd/C, 50% water wet, 0.546 g) was added to the mixture, followed by sodium acetate (2.06 g) and water (5.97 g). The reaction mixture was heated to 40° C. before pressurising the reaction vessel with hydrogen (5 bar). The reaction mixture was stirred at 40° C. under 5 bar hydrogen for 7 hours before being cooled to ~21° C. for a further 15 hours. The hydrogenation reaction mixture was then diluted with saturated aqueous sodium bicarbonate solution (9.5 mL) before being filtered through Celite®. The filter was washed with water (1.59 mL) and toluene (2×100 mL).

A portion of the crude product was purified by column chromatography on silica gel and analysed by chiral column chromatography (Chiralcel OD-RH 150×4.6 mm column, 30° C., 1 ml/minute flow rate, 60:40 heptane:ethanol eluant, ~600 psi back-pressure). The results showed that ratio of the desired (2R,3S) enantiomer to the undesired (2S,3R) enantiomer was 97:3 (94% enantiomeric excess).

Under similar conditions, but utilising the ligand ((R$_P$)-1-[(R)-α-(dimethylamino)-2-(diphenylphosphino)benzyl]-2-diphenylphosphinoferrocene), an enantioselectivity of about 84% was observed (which corresponds to approximately 70% enantiomeric excess).

The biphasic mixture was then allowed to separate for 10 minutes before the aqueous layer was discarded. The toluene layer was then washed with water (10 mL) before being concentrated in vacuo to ~45 mL. The toluene solution (containing voriconazole API—(2R,3S)-2-(2,4-difluorophenyl)-3-(5-fluoropyrimidin-4-yl)-1-(1H-1,2,4-triazol-1-yl)butan-2-ol) was heated to 45° C. and then treated with a solution of camphor sulfonic acid (CSA) (1.40 g) in acetone (40 mL) over 60 minutes. The resulting solution was then cooled to 5° C. over 60 minutes before being stirred for a further 120 minutes. The solids were then isolated, washed with toluene (2×20 mL) and dried for 18 hours under reduced pressure to give (2R,3S)-2-(2,4-difluorophenyl)-3-(5-fluoropyrimidin-4-yl)-1-(1H-1,2,4-triazol-1-yl)butan-2-ol ((1R,4R)-7,7-dimethyl-2-oxobicyclo[2.2.1]heptan-1-yl)methanesulfonate (2.52 g, 43% based on the pyrimidine starting material).

To the dried (2R,3S)-2-(2,4-difluorophenyl)-3-(5-fluoropyrimidin-4-yl)-1-(1H-1,2,4-triazol-1-yl)butan-2-ol ((1R,4R)-7,7-dimethyl-2-oxobicyclo[2.2.1]heptan-1-yl)methanesulfonate (2.52 g) was added an EtOH/acetone solution (3:1 ratio, 22 mL). The slurry was then heated to 50° C. for 30 minutes before cooling to 5° C. for 60 minutes. The solid was then isolated and dried for 24 hours at 40° C. under reduced pressure to give (2R,3S)-2-(2,4-difluorophenyl)-3-

(5-fluoropyrimidin-4-yl)-1-(1H-1,2,4-triazol-1-yl)butan-2-ol ((1R,4R)-7,7-dimethyl-2-oxobicyclo[2.2.1]heptan-1-yl)methanesulfonate as a white solid (2.39 g, 41.0% yield based on the pyrimidine starting material).

$^1$H NMR (400 MHz, CDCl$_3$): δ (ppm)=9.42 (1H, s, ArH), 9.10 (1H, s, ArH), 8.67 (1H, s, ArH), 8.14 (1H, s, ArH), 7.49 (1H, m, ArH), 7.53-7.42 (2H, m, 2×ArH), 4.96 (1H, d, CH$_2$), 4.48 (1H, d, CH$_2$), 4.11 (1H, sept, CH), 3.25 (1H, d, CH$_2$), 2.81 (1H, d, CH$_2$), 2.56-2.41 (1H, m, CH$_2$), 2.38-2.25 (1H, m, CH$_2$), 2.11-1.95 (2H, m, CH$_2$), 1.90 (1H, d, CH$_2$), −1.86-1.73 (1H, m, CH$_2$), 1.45-1.35 (1H, m, CH$_2$), 1.15 (3H, d, CH$_3$), 1.03 (3H, s, CH$_3$), 0.82 (3H, s, CH$_3$).

Step 2

To (2R,3S)-2-(2,4-difluorophenyl)-3-(5-fluoropyrimidin-4-yl)-1-(1H-1,2,4-triazol-1-yl)butan-2-ol ((1R,4R)-7,7-dimethyl-2-oxobicyclo[2.2.1]heptan-1-yl)methanesulfonate (2.125 g) was added EtOH (3.8 mL) and water (3.8 mL). The slurry was heated to 32.5° C. which resulted in an almost colourless solution. This solution was then added in small aliquots (1 mL) to a chilled (0° C.) solution of sodium acetate (0.30 g) in water (4.1 mL) over 45 minutes. To the resulting slurry was then added a solution of EtOH (0.45 mL) and water (0.45 mL). The mixture was then allowed to stir at 2° C. for 30 minutes before water (4.5 mL) was gradually added over 20 minutes. The slurry was then stirred at 2° C. for 13.5 hours before the solids were isolated and reslurried at 0-5° C. twice in water (6.4 mL). The isolated solid was then dried at 45° C. for ~48 hours at reduced pressure to give (2R,3S)-2-(2,4-difluorophenyl)-3-(5-fluoropyrimidin-4-yl)-1-(1H-1,2,4-triazol-1-yl)butan-2-ol as a white solid (0.969 g, 76% yield).

$^1$H NMR (400 MHz, CDCl$_3$): δ (ppm)=8.95 (1H, s, ArH), 8.61 (1H, s, ArH), 8.10 (1H, s, ArH), 7.62-7.56 (1H, m, ArH), 7.25 (1H, s, ArH), 6.90-6.79 (2H, m, 2×ArH), 6.50 (1H, br s, OH), 4.76 (1H, d, CH$_2$), 4.37 (1H, d, CH$_2$), 4.14 (1H, sept, CH), 1.11 (3H, d, CH$_3$).

EXAMPLE 2

Preparation of Voriconazole

To a mixture of CuF(PPh$_3$)$_3$ methanol solvate (0.0038 g) and (S)-1-{(S$_P$)-2-[2-(diphenylphosphino)phenyl]ferrocenyl}ethylbis[3,5-bis-(trifluoromethyl)phenyl]phosphine (0.0187 g) was added 3-methyl-3-pentanol (0.5 mL). The mixture was stirred at room temperature under an atmosphere of argon for 20 minutes until all solids were dissolved. The resulting solution was then cooled to 0° C. before 5-fluoro-4-vinylpyrimidine (0.050 g, limiting reagent) and 1-(2,4-difluorophenyl)-2-(1H-1,2,4-triazol-1-yl)ethanone (0.0899 g) in 3-methyl-3-pentanol (2 mL) were added. To this mixture at 0° C. was then added a solution of phenylsilane (0.0436 g) in 3-methyl-3-pentanol (0.5 mL) over about 30 minutes.

The reaction mixture was allowed to stir at 0° C. for 21 hours until complete consumption of 5-fluoro-4-vinylpyrimidine was observed by HPLC. The analysed reaction mixture was found to contain the desired product ((2R,3S)-2-(2,4-difluorophenyl)-3-(5-fluoropyrimidin-4-yl)-1-(1H-1,2,4-triazol-1-yl)butan-2-ol) in approximately 40% yield (based on pyrimidine starting material).

EXAMPLE 3

Preparation of Voriconazole

Using a similar procedure to that described in Example 2 with CuF(PPh$_3$)$_3$.MeOH as the copper catalyst, (S)-1-{(S$_P$)-2-[2-(diphenylphosphino)phenyl]ferrocenyl}ethylbis[3,5-bis-(trifluoromethyl)phenyl]phosphine as the chiral phosphine ligand and 2-methyl-2-butanol as the solvent gave voriconazole in 70% enantiomeric excess.

Using similar conditions but with ((R$_P$)-1-[(R)-α-(Dimethylamino)-2-(diphenylphosphino)benzyl]-2-diphenylphosphinoferrocene) as the chiral phosphine ligand an enantiomeric excess of 50% was achieved.

EXAMPLE 4

Preparation of A Voriconazole Precursor

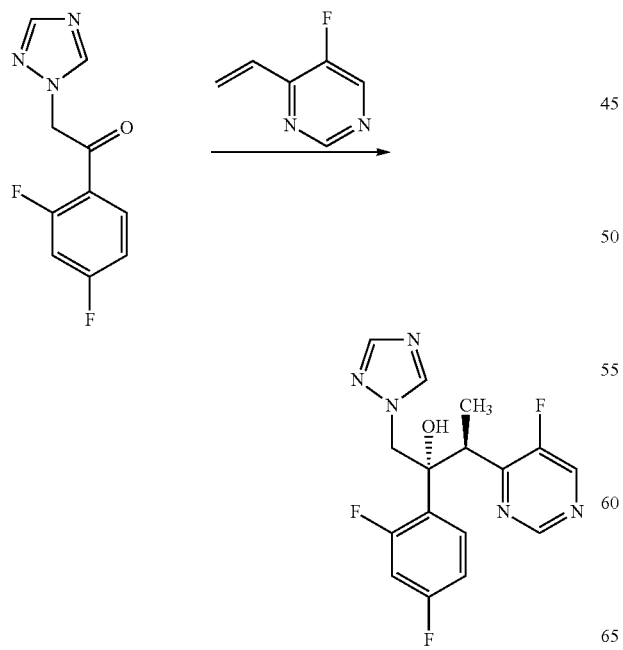

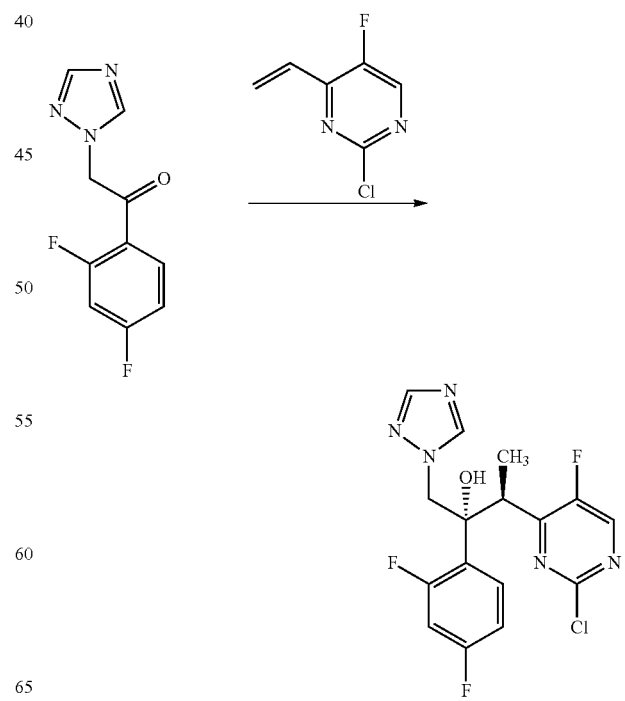

To a mixture of CuF(PPh$_3$)$_3$ methanol solvate (0.0029 g) and (R$_P$)-1-[(R)-α-(dimethylamino)-2-(diphenylphosphino)benzyl]-2-diphenylphosphinoferrocene (0.0108 g) was added n-butyl acetate (1 mL). The mixture was stirred at room temperature under an atmosphere of argon for 30 minutes until all solids were dissolved. The resulting solution was then cooled to 0° C. before 2-chloro-5-fluoro-4-vinylpyrimidine (0.050 g, limiting reagent) and 1-(2,4-difluorophenyl)-2-(1H-1,2,4-triazol-1-yl)ethanone (0.074 g) in n-butyl acetate (1 mL) were added. To this mixture at 0° C. was then added a solution of phenylsilane (0.034 g) in n-butyl acetate (0.25 mL) over about 5 minutes.

The reaction mixture was allowed to stir at 0° C. for 24 hours until complete consumption of 2-chloro-5-fluoro-4-vinylpyrimidine was observed. The reaction mixture was analysed by HPLC and was found to contain the desired product ((2R,3S)-3-(2-chloro-5-fluoropyrimidin-4-yl)-2-(2,4-difluorophenyl)-1-(1H-1,2,4-triazol-1-yl)butan-2-ol) in approximately 5% yield.

EXAMPLE 5

Preparation of A Voriconazole Intermediate

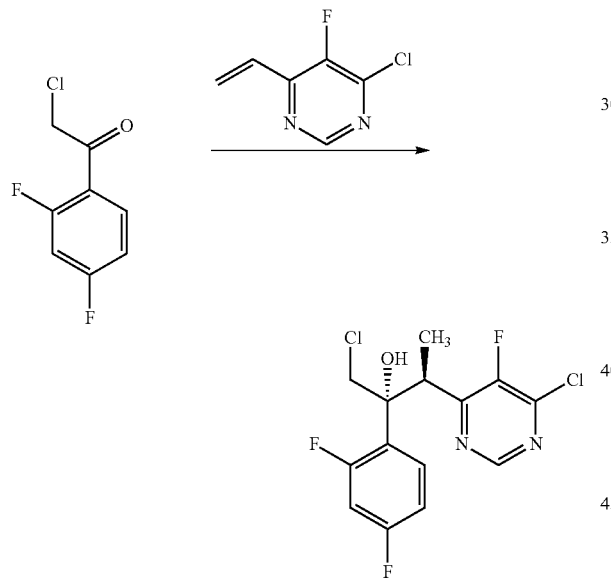

To CuF(PPh$_3$)$_3$ methanol solvate (0.0094 g) and (R$_P$)-1-[(R)-α-(dimethylamino)-2-(diphenylphosphino)benzyl]-2-diphenylphosphinoferrocene (0.0068 g) under argon was added tetrahydrofuran (1 mL). The mixture was stirred at 20° C. (under argon) for 30 minutes until all solids were dissolved. The solution was then cooled to −20° C. and phenyl silane (0.027 g) was added. After 10 minutes, a solution of 4-chloro-5-fluoro-6-vinylpyrimidine (0.180 g) and 2-chloro-1-(2,4-difluorophenyl)ethanone (0.095 g) in tetrahydrofuran (1.5 mL) was added over approximately 5 minutes. The reaction mixture was stirred for 1 hour at −20° C. until complete consumption of the vinyl pyrimidine was observed by HPLC analysis. The reaction was quenched by addition of aqueous ammonium chloride (1 M, 3 mL), followed by methyl tert-butyl ether (5 mL). The organic layer was dried to a residue which was then subjected to purification by column chromatography (eluting with 0-20% ethyl acetate in cyclohexane) to give (2R,3S)-1-chloro-3-(6-chloro-5-fluoropyrimidin-4-yl)-2-(2,4-difluorophenyl)butan-2-ol (0.259 g, 65% yield) as a white solid.

$^1$H NMR (500 MHz, CDCl$_3$): δ (ppm)=8.71 (1H, s, ArH), 7.75 (1H, m, ArH), 6.90 (1H, m, ArH), 6.78 (1H, m, ArH), 5.51 (1H, S, OH), 4.00 (1H, sept, CH), 3.94 (1H, d, CH$_2$), 3.51 (1H, d, CH$_2$), 1.08 (3H, d, CH$_3$).

Chiral HPLC analysis (Chiralcel-OJ-H, with 95:5 Hexane:IPA, at 1 ml/min) of product demonstrated an enantioselectivity of ~95.7% in the reductive aldol reaction (~91% e.e)

EXAMPLE 6

Preparation of a Voriconazole Intermediate

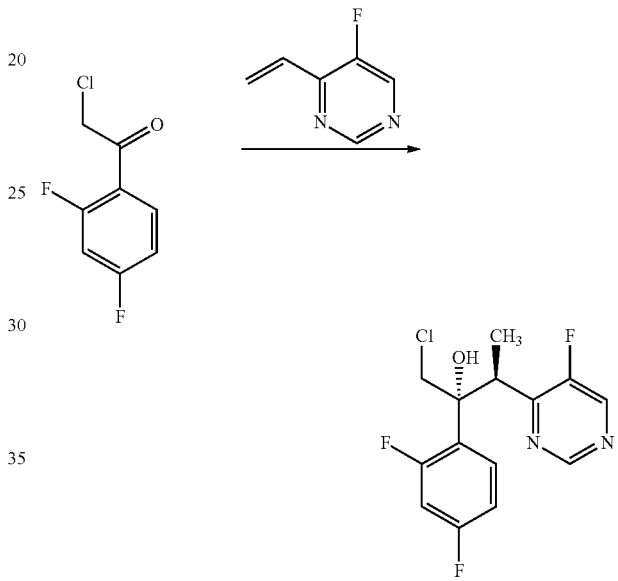

To CuF(PPh$_3$)$_3$ methanol solvate (0.137 g) and (R$_P$)-1-[(R)-α-(dimethylamino)-2-(diphenylphosphino)benzyl]-2-diphenylphosphinoferrocene (0.100 g) was added tetrahydrofuran (14 mL). The mixture was stirred at 0-5° C. (under argon) for 30 minutes until all solids were dissolved. To this solution was then added phenyl silane (0.789 g). After 10 minutes, a solution of 5-fluoro-4-vinylpyrimidine (0.903 g) and 2-chloro-1-(2,4-difluorophenyl)ethanone (1.68 g) in tetrahydrofuran (22 mL) was added over 30 minutes. The reaction mixture was stirred for 1 hour at 0-5° C. after which no further 5-fluoro-4-vinylpyrimidine was observable by HPLC. The reaction was quenched by addition of aqueous ammonium chloride (1 M, 15 mL), followed by methyl tert-butyl ether (30 mL). The organic layer was dried to a residue which was then subjected to purification by column chromatography (eluting with 5-40% ethyl acetate in cyclohexane) to give (2R,3S)-1-chloro-2-(2,4-difluorophenyl)-3-(5-fluoropyrimidin-4-yl)butan-2-ol as a white solid (1.70 g, 74% yield).

$^1$H NMR (500 MHz, CDCl$_3$): δ (ppm)=8.93 (1H, s, ArH), 8.57 (1H, m, ArH), 7.76 (1H, m, ArH), 6.90 (1H, m, ArH), 6.78 (1H, m, ArH), 5.79 (1H, S, OH), 3.97 (1H, sept, CH), 3.93 (1H, d, CH$_2$), 3.49 (1H, d, CH$_2$), 1.05 (3H, d, CH$_3$).

Chiral HPLC analysis (Cellulose-1 column, using 60:40 acetonitrile:water ratio eluant at at 1 mL/min & 25° C.) of the (2R,3S)-1-chloro-2-(2,4-difluorophenyl)-3-(5-fluoropyrimidin-4-yl)butan-2-ol product demonstrated an enantioselectivity of ~93.2% in the reductive aldol reaction (~86% enantiomeric excess).

The following Preparations show how vinyl heteroaryl starting materials may be prepared.

Preparation 1—4-Chloro-5-fluoro-6-vinyl pyrimidine

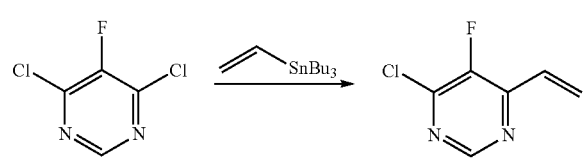

A mixture of 4,6-dichloro-5-fluoropyrimidine (5.0 g, 30.0 mmol, 1.0 equiv) and tributyl(vinyl)tin (10.4 g, 33.0 mmol, 1.1 equiv) in dichloromethane (50 mL) was degassed with a stream of with nitrogen for 10 minutes. Bis(triphenylphosphine) palladium(II) chloride (0.53 g, 0.75 mmol, 0.025 equiv) was added. The resulting mixture was degassed with a stream of nitrogen for an additional 15 minutes and heated at reflux for 72 hours. The reaction mixture was cooled to room temperature and quenched with an aqueous potassium fluoride solution (2 M, 75 mL, 5 equiv). The resulting mixture was allowed to stir for 2 hours and filtered through Celite®. The filtrate was poured into a separatory funnel and separated. The organic layer was washed with water (20 mL) and saturated brine (20 mL), dried over sodium sulfate, filtered and concentrated under reduced pressure at 20° C. The resulting crude product was purified on an AnaLogix® (SF40-115 g) column. The gradient utilized for the purification was 10 minutes isocratic pentane, followed by a 20 minutes ramp to 5% diethyl ether in pentane. The pure fractions were combined and concentrated under reduced pressure at 20° C. to give 4-chloro-5-fluoro-6-vinylpyrimidine (3.0 g, 63% yield).

Mass spectrum (positive mode): m/z 158.0 (M+). $^1$H NMR (300 MHz, CDCl$_3$): δ (ppm) 8.71 (s, 1H), 6.99 (m, 1H), 6.75 (dd, J=17.4 Hz, 1.8 Hz, 1H), 5.90 (dd, J=10.5 Hz, 1.5 Hz, 1H). $^{19}$F NMR (282 MHz, CDCl$_3$): δ 133.88 (s).

Preparation 2—4-Chloro-5-fluoro-6-vinyl pyrimidine, alternative route

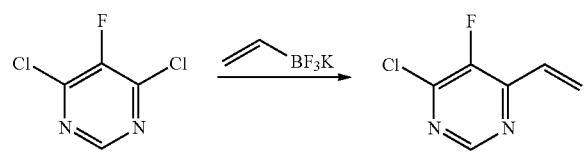

4,6-Dichloro-5-fluoropyrimidine (6 g, 36.0 mmol) was reacted with potassium vinyl trifluoroborate (1.60 g, 37.8 mmol, 1.05 eq), and caesium carbonate (17.58 g, 1.5 eq) in water/methyl tetrahydrofuran. The reaction was treated with Pd(PPh$_3$)$_2$Cl$_2$ (504 mg, 0.02 eq) and PPh$_3$ (189 mg, 0.02 eq) under argon. The reaction was heated to reflux and held under reflux for 20 hours. The reaction was quenched by the addition of further water and tert-butyl methyl ether. The organic phase was atmospherically distilled to remove the solvents. The residue was purified by column chromatography, 12-100% dichloromethane in hexane. The combined fractions were concentrated by fractional distillation to give 4.1 g (71% yield) of the product as a slightly yellow oil.

Preparation 3—4-Chloro-5-fluoro-6-vinyl pyrimidine, alternative route

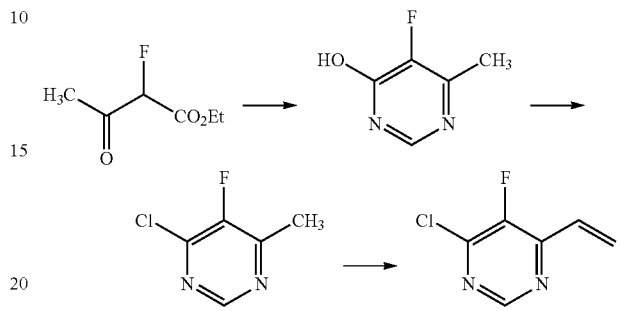

Step 1

Sodium methoxide (151.6 g, 2.81 moles) was added portionwise to methanol (1.75 L), keeping the temperature below 30° C. using an ice/methanol cooling bath. Formamidine acetate (146.12 g, 1.40 moles) was added in one portion. The mixture was cooled to 5° C. and then ethyl fluoroacetoacetate (218.3 g, 1.47 moles) was added over 10 minutes with cooling. The reaction mixture was warmed to 25° C. and stirred at this temperature for 2 hours. Acetic acid (252.8 g, 4.21 moles) was added to the mixture over 5 minutes and then the solvents were evaporated. Toluene (400 mL) was then added and the resulting slurry was concentrated by evaporation again. Ethyl acetate (808 mL) was added to the resulting slurry and the mixture was warmed to 40° C. for 15 minutes. The insoluble material was filtered off and washed with ethyl acetate (2×153 mL).

The filtrate was evaporated and the resulting slurry began to solidify on standing. Diethyl ether (400 mL) was added and the solid mass was broken up. After 4 hours at room temperature the solid product was filtered off and washed with diethyl ether (2×150 mL). After drying in a warm oven overnight, 4-hydroxy-5-fluoro-6-vinylpyrimidine was obtained as a waxy solid, 264.6 g (147%). Proton NMR showed that the required product contained 0.86 molar eq. of sodium acetate (yield adjusted for sodium acetate=94.9%).

Step 2

4-Hydroxy-5-fluoro-6-vinylpyrimidine (954.2 g, crude product of step 1, 4.80 moles) was added portionwise over 15 minutes to phosphorus oxychloride (1622 mL, 986 g, 6.43 moles, 1.7 vol) keeping the temp at 40° C. with ice bath cooling. The cooling was removed and the temperature rose to 50° C. The reaction was kept at 50° C. for 15 minutes and then heated at 80° C. for two hours. During this time all solids dissolved to give a brown solution.

The resulting solution was added dropwise, over 90 minutes, with vigorous stirring, to water (7.35 L), keeping the temperature at 20° C. with ice/methanol cooling and by controlling the rate of addition. The reaction was stirred at 20° C. for a further 30 minutes. Salt (NaCl) was added until the solution was saturated and the mixture was extracted with dichloromethane (3.63 L followed by 6×1.8 L). The dichloromethane extracts were washed with saturated sodium bicarbonate solution (363 mL), dried over MgSO$_4$ and concentrated to give a pale brown oil. The oil was distilled at 180 millibars pressure. 4-Chloro-5-fluoro-6-methylpyrimidine distilled in the range 100-106° C. at this pressure.

Step 3

To a solution of N-isopropyl-N-methylenepropan-2-aminium chloride (13.3 g, 88.7 mmol) in acetonitrile (55 mL) was added 4-chloro-5-fluoro-6-methylpyrimidine (10.0 g, 68.2 mmol). The reaction flask was flushed with argon and the mixture was heated at reflux for 24 hours with stirring, then cooled to room temperature. Water (130 mL) was added and the mixture was extracted with dichloromethane (140 mL). The organic phase was washed with 10% aqueous $KHSO_4$ (400 mL) and dried over $Na_2SO_4$. The solution was filtered and evaporated in vacuo at 300 millibar pressure and 35° C. tert-Butylcatechol (30 mg, 0.2 wt %, based on the mass of the crude material) was added. Residual solvent was removed under vacuum at 50° C. and the crude product was then distilled at 5 millibar pressure and 50° C. (oil bath). tert-Butylcatechol (0.1 wt %) was added to the distilled 4-chloro-5-fluoro-6-vinyl pyrimidine (7.9 g, 73%) which was obtained as a slightly yellow oil.

Preparation 4—5-Fluoro-4-vinylpyrimidine

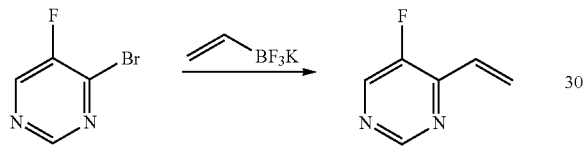

4-Bromo-5-fluoropyrimidine (5 g) was reacted with potassium vinyltrifluorborate (1.05 equivalents) in the presence of $(PPh_3)_2PdCl_2$ (0.02 eq), $PPh_3$ (0.02 eq), and $Cs_2CO_3$ (3 equivalents) in a mixture of methyl tetrahydrofuran (85 ml) and water (8.5 ml). The reaction was heated at 75° C. for about 5.5 hours. The reaction mixture was then diluted with methyl tert-butyl ether (50 ml), followed by aqueous extraction. The crude product was purified by distillation at 170 mbar (90-110° C.). The product was obtained as a colourless oil (1.44 g, 41% yield).

Mass Spectrum (positive mode): m/z 124.0 (M+). $^1$H NMR (300 MHz, $CDCl_3$): δ (ppm) 8.98 (s, 1H), 6.96 (dd, 1H), 6.70 (m, 1H), 5.82 (d, 1H). $^{19}$F NMR (282 MHz, $CDCl_3$): 138.60 (s).

Preparation 5—2-Chloro-5-fluoro-4-vinylpyrimidine

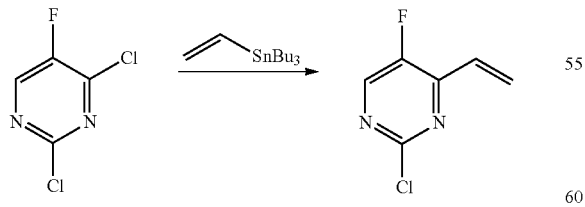

A mixture of 2,4-dichloro-5-fluoropyrimidine (5.0 g, 30.0 mmol, 1.0 equiv), tributyl(vinyl)tin (10.4 g, 33.0 mmol, 1.1 equiv) in dichloromethane (50 mL) was degassed with a stream of nitrogen for 10 minutes. Bis(triphenylphosphine) palladium(II) chloride (0.53 g, 0.75 mmol, 0.025 equiv) was added. The resulting mixture was degassed with a stream of nitrogen for an additional 15 minutes and heated at reflux for 24 hours. The reaction mixture was cooled to room temperature and quenched with an aqueous potassium fluoride solution (2 M, 75 mL, 5 equiv). The resulting mixture was allowed to stir for 2 hours and filtered through Celite®. The filtrate was poured into a separatory funnel and separated. The organic layer was washed with water (20 mL) and saturated brine (20 mL), dried over sodium sulfate, filtered and concentrated under reduced pressure at 20° C. The resulting crude product was purified on an AnaLogix® (SF40-115 g) column. The gradient utilized for the purification was 10 minutes isocratic pentane, followed by a 20 minutes ramp to 5% diethyl ether in pentane. The pure fractions were combined and concentrated under reduced pressure at 20° C. to give 2-chloro-5-fluoro-4-vinylpyrimidine as an oil (3.65 g, 77% yield).

The invention claimed is:

1. A process for preparing a compound of the formula:

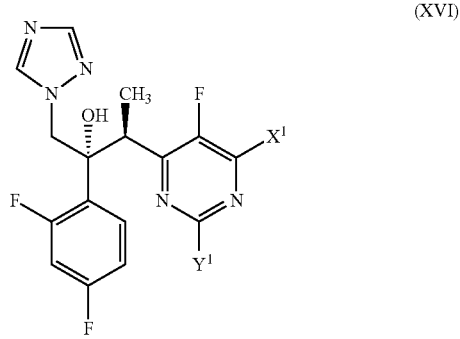

(XVI)

wherein $X^1$ and $Y^1$ are both H or one of $X^1$ and $Y^1$ is H and the other is chloro;

by reacting a compound of formula:

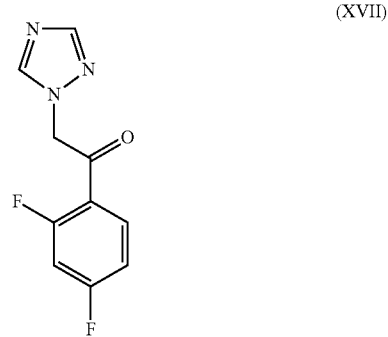 [SMILES: O=C(Cn1cncn1)c1ccc(F)cc1F]

(XVII)

with a compound of formula:

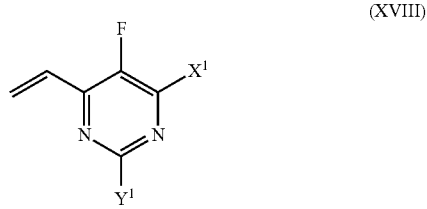

(XVIII)

wherein $X^1$ and $Y^1$ are as defined above, in the presence of a copper catalyst, a chiral phosphine ligand and a reducing agent.

2. A process as claimed in claim 1 in which $X^1$ is chloro and $Y^1$ is H.

3. A process as claimed in claim 1 wherein the catalyst is a copper(I) catalyst.

4. A process as claimed in claim 1 wherein the catalyst is $CuF(PPh_3)_3$.methanol solvate or $CuF(PPh_3)_3$.ethanol solvate.

5. A process as claimed in claim 1 wherein the ligand is (S)-1-{($S_P$)-2-[2-(diphenylphosphino)phenyl]ferrocenyl}ethylbis[3,5-bis-(trifluoromethyl)phenyl]phosphine.

6. A process as claimed in claim 1 wherein the reducing agent is phenysilane.

7. A process as claimed in claim 1 wherein the temperature of the reaction is about −9° C.

8. A process as claimed in claim 1 wherein the product is voriconazole or the product is further transformed in one or more steps to provide voriconazole.

9. A process as claimed in claim 1 wherein a tertiary alcohol is present.

10. A process as claimed in claim 9 wherein the reaction is performed as a solution in 2-methyl-2-butanol.

* * * * *